(12) United States Patent
Chiueh et al.

(10) Patent No.: US 7,592,162 B2
(45) Date of Patent: Sep. 22, 2009

(54) DETECTION METHOD FOR DIFFERENTIATING BETWEEN CHICKEN-DERIVED INGREDIENTS AND EGG-DERIVED INGREDIENTS IN PRODUCTS

(76) Inventors: Lih-Ching Chiueh, No. 161-2, Kunyang St., Nangang District, Taipei City (TW) 115-61; Shiou-Wei Tsuei, No. 161-2, Kunyang St., Nangang District, Taipei City (TW) 115-61; Pei-Chun Hsieh, No. 161-2, Kunyang St., Nangang District, Taipei City (TW) 115-61; Tsung-Hsi Wu, No. 161-2, Kunyang St., Nangang District, Taipei City (TW) 115-61; Yang-Chih Shih, No. 161-2, Kunyang St., Nangang District, Taipei City (TW) 115-61; Shu-Kong Chen, No. 161-2, Kunyang St., Nangang District, Taipei City (TW) 115-61

( * ) Notice: Subject to any disclaimer, the term of this patent is extended or adjusted under 35 U.S.C. 154(b) by 0 days.

(21) Appl. No.: 11/963,605

(22) Filed: Dec. 21, 2007

(65) Prior Publication Data

US 2008/0254463 A1    Oct. 16, 2008

(30) Foreign Application Priority Data

Apr. 14, 2007    (TW) ............................. 96113211 A

(51) Int. Cl.
*C12Q 1/68* (2006.01)
*C12P 19/34* (2006.01)
(52) U.S. Cl. .......................... 435/91.2; 435/6; 435/91.1
(58) Field of Classification Search .................... None
See application file for complete search history.

(56) References Cited

U.S. PATENT DOCUMENTS

2006/0099617 A1* 5/2006 Shih et al. ..................... 435/6

* cited by examiner

*Primary Examiner*—Young J Kim
(74) *Attorney, Agent, or Firm*—WPAT, P.C.; Anthony King; Kay Yang

(57) ABSTRACT

The present invention relates to a detection method to differentiate between egg-derived ingredients and chicken-derived ingredients (chicken parts/tissues, excluding eggs) in foods or other products and primer pairs and probes used for specifically detecting chicken in foods or products.

5 Claims, 8 Drawing Sheets

DETECTION METHOD FOR DIFFERENTIATING BETWEEN CHICKEN-DERIVED INGREDIENTS AND EGG-DERIVED INGREDIENTS IN PRODUCTS

FIELD OF THE INVENTION

The present invention relates to a detection method to differentiate between egg-derived ingredients and chicken-derived ingredients (chicken parts/tissues, excluding eggs) in foods or other products and primer pairs and probes used for specifically detecting chicken in foods or products.

BACKGROUND OF THE INVENTION

For reasons such as religion, health, economy and ecological conservation, vegetarians or people who prefer vegetarian diets have become a big part of the population, creating great business opportunities in such food industry. In recent years, some unlawful businesses violate consumers' rights by adding animal-derived ingredients in food products for better tastes and lower costs. In order to protect consumers' rights and prevent unlawful profits by these businesses, the Bureau of Food and Drug Analysis in Taiwan started research and development for methods to detect animal-derived ingredient in food products in 2004. The Bureau of Food and Drug Analysis also conducts surveys and accepts complaints from the consumers. Detection methods can be used to determine the presence of animal-derived ingredients and differentiate the origins thereof (such as pork, beef, chicken, fish and others) in food products. The present invention has been submitted in a patent application in Taiwan (ROC (Taiwan) Patent Application Number 093128997) and is now being examined. Since there is no definite guideline for vegetarian diets, vegetarian food makers use different standards to manufacture their products. In fact, although most vegetarians can accept eggs and milk as part of their diets, it is still critical to differentiate between chickens and eggs in vegetarian food products for those who are strictly vegan. Such detection method can provide adequate consumer protection and also prevent unlawful business conducts in the industry of vegetarian food manufacture.

In general, morphology and specificity to components, such as proteins or DNAs, can be used to identify species. Different tissues or organs within a species are identified by the overall appearance of an organ, cells that form a tissue and specific components of a tissue. However, the appearance and cells of food ingredients (for example, meat, basically composed of muscle tissues) are usually destroyed after being processed, and are therefore unidentifiable in highly processed foods. Thus, detection of specific molecules in tissues should be the general method to identify the origins of ingredients in these food products. A specific DNA sequence can be detected to identify species. For example, in Meat Sci. 53:227-231, specific primer pairs were designated to identify the gene of chicken actin where PCR was performed. In addition, Poultry Science 83:2083-2085 disclosed several specific primer pairs designated for ATPase subunit 8 genes. Although patent application Ser. No. 093128997 presented a detection method for identifying animal-derived ingredients in food products using specific primer pair and probe designated from highly conserved DNA sequence of animal in real time PCR, this invention merely identified the origins of ingredients in food. Because DNAs in different organs and tissues are identical for a single species, if one wishes to differentiate the ingredients from different tissues of the same species, the above detection method, which uses the DNA sequence specific to species, is not able to do that.

Although DNAs of different tissue cells are identical within a species, they have "tissue specific expression" and the proteins of such "tissue specific expression" can be targeted to distinguish the tissue cells from different origins within a species. This method has been disclosed in Shokuhin Eiseigaku Zasshi (J. Food Hyg. Soc. Japan) 47(4): 189-195, Shokuhin Eiseigaku Zasshi 43(4): J275-J279 and Allergy 54(5): 464-472, which uses antigens or allergens, such as ovalbumin in eggs, to detect egg ingredient in food products. However, according to the research report in Shokuhin Eiseigaku Zasshi (J. Food Hyg. Soc. Japan) 47(4): 189-195, the detection method by using tissue specific expression may produce false positive result because of cross-reaction, so it cannot accurately differentiate between chicken- and egg-derived ingredients in food.

For the above reasons, no prior art can be used to differentiate (or accurately differentiate) between chicken- and egg-derived ingredients in food. Hence, there is still a need for a precise detection method.

SUMMARY OF THE INVENTION

The invention provides a detection method to differentiate chicken-derived and egg-derived ingredients in food or products, said method comprising using a highly conserved chromosomal gene and a highly conserved mitochondrial gene in chicken as templates to design specific primer pairs and hybridized probes, performing PCR and real time PCR to analyse the difference in DNA amount between the chromosomal gene and the mitochondrial gene in samples; wherein if the result shows that only the mitochondrial gene but not the chromosomal gene is detected, it means that the food or other product only contains egg-derived ingredients, and if the mitochondrial gene and the chromosomal gene are both detected, it means that the food or product contains chicken-derived ingredients.

The invention also provides primer pairs for specificity designated for growth hormone gene and 12S ribosomal RNA gene in chicken, and the probes hybridizing to growth hormone gene and 12S ribosomal RNA gene in chicken.

Lane 8: meringue 3; Lane 9: meringue 4; Lane 10: meringue 5; Lane 11: egg white powder.

Figure 6:
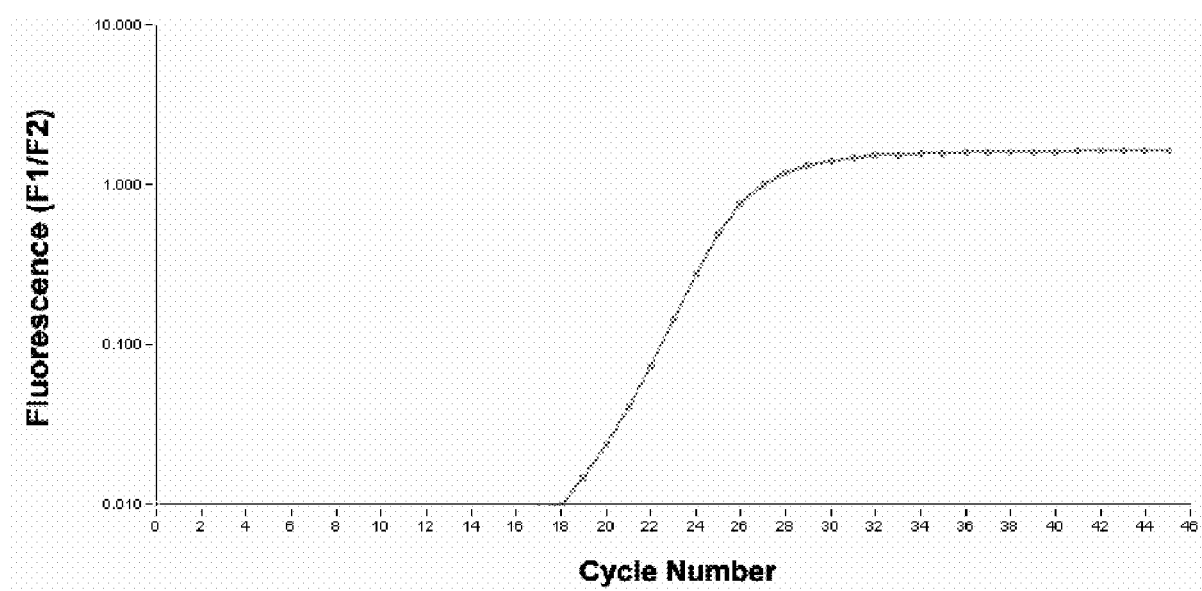

FIG. 6 shows the results of the detection of chicken, egg, commercial meringue and commercial egg white powder by specified growth hormone probe.

Figure 7:
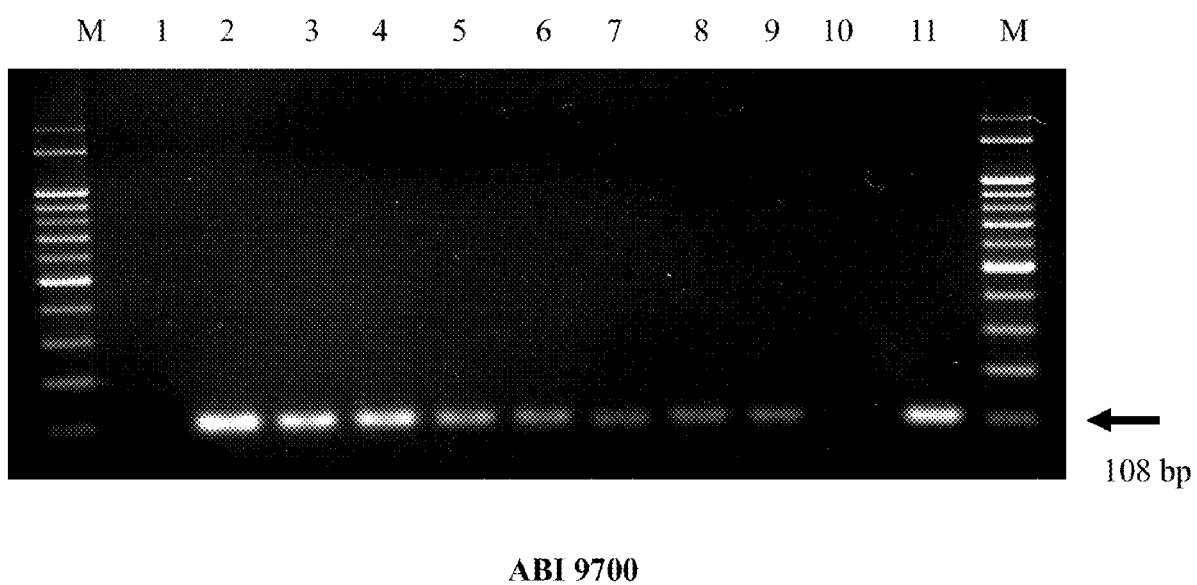

FIG. 7 shows the results of the detection of chicken, egg, commercial meringue and commercial egg white powder by specified 12S rRNA primer. M: 100 bp marker; Lane 1: NTC; Lane 2: chicken; Lane 3: egg; Lane 4: yolk; Lane 5: egg white; Lane 6: meringue 1: Lane 7: meringue 2; Lane 8: meringue 3; Lane 9: meringue 4; Lane 10: meringue 5; Lane 11: egg white powder.

Figure 8:
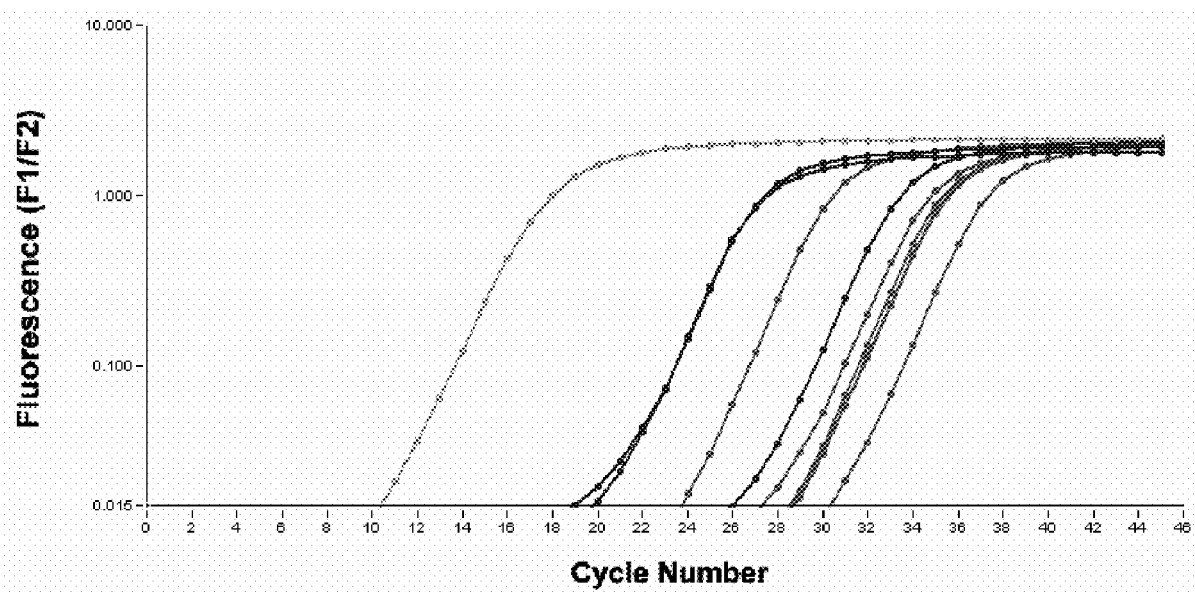

FIG. 8 shows the results of the detection of chicken, egg, commercial meringue and commercial egg white powder by specified 12S rRNA probe.

DETAILED DESCRIPTION OF THE INVENTION

The present invention relates to a detection method to differentiate between egg-derived ingredients and chicken-derived ingredients (chicken parts/tissues, excluding eggs) in foods or products and primer pairs and probes used for specifically detecting chicken-derived ingredients in foods or other products.

The invention provides a detection method to differentiate chicken-derived and egg-derived ingredients in food or products, said method comprising using a highly conserved chromosomal gene and a highly conserved mitochondrial gene in chicken as templates to design specific primer pairs and hybridized probes, performing PCR and real time PCR to analyse the difference in DNA amount between the chromosomal gene and the mitochondrial gene in samples; wherein if the result shows that only the mitochondrial gene but not the chromosomal gene is detected, it means that the food or other product only contains egg-derived ingredients, and if the mitochondrial gene and the chromosomal gene are both detected, it means that the food or product contains chicken-derived ingredients.

The term "chicken" as used herein refers to the ingredients from chicken other than eggs. The term "egg" as used herein refers to eatable eggs either fertilized or non-fertilized.

The invention utilizes the differences of the copy numbers of the chromosomal genome and mitochondrial genome as well as the differences in cell numbers to differentiate egg-derived and chicken-derived ingredients in food products. These differences result in significant difference in the amounts of a specific mitochondrial gene and a chromosomal gene in egg and chicken tissues.

The term "difference in copy numbers" as used herein refers to the different copy number of a specific chromosomal gene and a specific mitochondrial gene in a single cell. Genomes in eukaryotic cells include chromosomal genome and mitochondrial genome. The number of mitochondria in a single cell of eukaryote can be more than ten thousand; therefore the copy number of a mitochondrial gene can be more than ten thousand sets. In livestock, a single cell contains approximately 5,000 to 10,000 mitochondria (Science Development, Issue 405: 22-27); therefore, the copy numbers between a chromosomal gene and a mitochondrial gene can be as high as to ten thousand times ($10^4$).

The term "difference in cell number" as used herein refers to the different cell numbers of eggs and chicken tissues. Egg is a single cell or only has tissues containing few cells. That is, the cell number difference is about more than one million times ($10^6$) between an egg (average 55 grams) and other chicken tissues with the same mass and volume as the egg.

In light of the above facts and analysis, by choosing a single chromosomal gene and a single mitochondrial gene, observation of the difference in their copy numbers and the difference in cell numbers can be used to differentiate egg-derived and chicken tissues-derived ingredients in foods or products. Since an unfertilized egg is a single cell, if a chromosomal gene with low copy number is chosen, then the concentration of this DNA should also be rare. As a result, it is presumed that the DNA of such chromosomal gene cannot be amplified by PCR, or the amplification cannot be detected because of the less amplicons. On the other hand, there are several hundred to ten thousand of chosen mitochondrial genes in an egg, and the content of DNA is relatively high; thus the DNA can easily be detected. In other chicken parts/tissues (with same mass and volume with an egg), because cell numbers are high and so are their DNA amounts, DNA amplification can be easily detected through PCR even if only a single copy number of chromosomal gene is chosen. In other chicken parts/tissues, both the copy number of mitochondrial genome and cell number are high, so the mitochondrial DNA can definitely be detected through PCR. The egg-derived ingredients should be diluted in food, therefore making it harder to detect the chromosomal DNA. But it is still possible to detect the mitochondrial DNA because of the high copy number of the mitochondrial genome in an egg.

According to the invention, food or product samples are checked for both a chosen chromosomal gene and a chosen mitochondrial gene, and these gene are highly conserved in chicken and specific to chicken. If the result shows that only the mitochondrial DNA can be detected whereas the chromosomal gene is not able to be detected or compared to mitochondrial DNA the amount is very low, then such samples contain egg-derived ingredients only. If both chromosomal gene and mitochondrial gene are detected, then the samples contain chicken-derived ingredients (chicken tissues). It is also possible that these sample contain egg-derived ingredients at the same time.

In light of the above facts and analysis, the preferable way to differentiate samples that only contain egg-derived ingredient from samples that contain other chicken parts/tissues is to use the designed primer pairs and probes which specifically target the highly conserved chromosomal gene and mitochondrial gene in chicken, then perform real-time PCR and analyze the different amounts of the chromosomal gene and mitochondrial gene.

According to the invention, the highly conserved chromosomal gene in chicken refers to any gene generally derived from the highly conserved mitochondrial genes. It includes but is not limited to myostatin gene, growth hormone, satellite gene, beta-actin gene, myosin gene and hemoglobin gene. The preferred highly conserved chromosomal genes in chicken are selected from growth hormone gene, myostatin gene and beta-actin gene. The more preferred highly conserved chromosomal gene in chicken is growth hormone gene. According to the invention, the highly conserved mitochondrial gene in chicken refers to any gene generally derived from the highly conserved mitochondrial gene. It includes but is not limited to 12S rRNA gene, 16S rRNA gene, cytochrome b gene, ATPase subunit 8 gene and ATPase subunit 6 gene. The preferred highly conserved mitochondrial genes in chicken are 12S rRNA gene, 16S rRNA gene and cytochrome b gene. The more preferred highly conserved mitochondrial genome in chicken is 12S rRNA gene.

The invention can be carried out by checking DNA sequence database or gene library to confirm other general highly conserved DNA or DNA segments/sequence in chicken as the detection target. The preferable way to differentiate foods or other products that only contain egg-derived ingredients from foods or products that contain other chicken parts/tissues is to design primer pairs and probes which specifically target to the highly-conserved growth hormone gene and 12S rRNA gene in chicken, then use the above primer pairs and probes to perform real-time PCR and analyze the differences of DNA counts in growth hormone gene and 12S rRNA gene in the same samples.

According to the invention, the primer pairs and probes used in the method of the invention were designed to specifically target to the highly conserved chromosomal gene and mitochondrial gene. In order to design the primer pairs, sequencing and analysis were conducted repeatedly. Any primer pairs specific to highly conserved chromosomal gene and mitochondrial gene in chicken can be utilized in this invention. The preferred primer pairs of highly conserved chromosomal gene in chicken used in this invention are the ones specific to myostatin gene, growth hormone gene, satellite gene, beta-actin gene, myosin gene or hemoglobin gene. The more preferred primer pairs of highly conserved chromosomal gene in chicken used in this invention are those specific to growth hormone gene, myostatin gene, or beta-actin gene. The most preferred primer pair of highly conserved chromosomal gene in chicken used in this invention is the one specific to growth hormone gene. The preferred primer pairs of highly conserved mitochondrial gene in chicken used in this invention are the ones specific to 12S rRNA gene, 16S rRNA gene, cytochrome b gene, ATPase subunit 8 gene or ATPase subunit 6 gene. The more preferred primer pairs of highly conserved mitochondrial gene in chicken used in this invention are those specific to 12S rRNA gene, 16S rRNA gene or cytochrome b gene. The most preferred primer pair of highly conserved mitochondrial gene in chicken used in this invention is the one specific to 12S rRNA.

According to the invention, probes hybridizing highly conserved chromosomal gene and mitochondrial gene in chicken are needed to perform real-time PCR. Any probe that can perform the above-mentioned hybridization can be used in this invention. The preferred probes for highly conserved chromosomal gene in chicken are those hybridized with myostatin gene, growth hormone gene, satellite gene, beta-actin gene, myosin gene or hemoglobin gene. The more preferred probes for highly conserved chromosomal gene in chicken are those hybridized with myostatin gene, growth hormone gene or beta-actin gene. The most preferred probe for highly conserved chromosomal gene in chicken is the one hybridized with 12S rRNA gene. According to the invention, the preferred probes for highly conserved mitochondrial genome in chicken are those hybridized with 12S rRNA gene, 16S rRNA gene, cytochrome b gene, ATPase subunit 8 gene or ATPase subunit 6 gene. The more preferred probe for highly conserved mitochondrial gene in chicken are those hybridized with 12S rRNA gene, 16S rRNA gene or cytochrome b gene. The most preferred probe for highly conserved mitochondrial gene in chicken is the one hybridized with 12S rRNA gene.

The invention provides a primer pair that is specifically hybridized with growth hormone gene in chicken, with nucleotide sequences shown as 5'-TAACTTTTGTAAGCGGA-CACTCAT-3' (SEQ ID NO: 1) and 5'-GCATTACCT-GCGCTGTGGC-3' (SEQ IC NO: 2), and a probe that is specifically hybridized with growth hormone gene in chicken, with nucleotide sequences shown as 5'-CCTTCAG-GCTTGACAGTGACCTCCAG-3' (SEQ ID NO: 3). After DNA is obtained from food samples or other product samples, PCR or real-time PCR can be performed by using the above-mentioned primer pair or probe to examine whether any sample contains ingredients derived from chicken.

The invention provides a primer pair that is specifically hybridized with 12S rRNA in chicken, with nucleotide sequences shown as 5'-GAGTGGCCACATGTTATCTGC-3' (SEQ ID NO: 4) and 5'-TAATCGTTGAGGCTAAGATGG-3' (SEQ ID NO: 5), and a probe that is specifically hybridized with 12S rRNA in chicken, with nucleotide sequences shown as 5'-AGCCTAAGATCCACCTAAACCCAACCCA-3' (SEQ ID NO: 6). After DNA is obtained from food samples or other product samples, PCR or real-time PCR can be performed by using the above mentioned primer pair or probe to examine whether any sample contains ingredients derived from chicken.

According to the invention, comparison of the growth hormone gene amount resulted from real time PCR with sample DNA using primer pair SEQ ID NO: 1, SEQ ID NO: 2 and probe SEQ ID NO: 3 and the 12S rRNA gene amount resulted from real time PCR with sample DNA using primer pair SEQ ID NO: 4, SEQ ID NO: 5 and probe SEQ ID NO: 6 can successfully identify whether a sample only contains egg-derived ingredients or other ingredients from chicken tissues.

EXAMPLE

Example 1

Detection by Using Chicken Specific Primers and Probes

Samples

The samples tested in the example are DNAs extracted from 14 species, including cow, hog, kangaroo, sheep, horse, deer, chicken, turkey, goose, ostrich, duck, rabbit, swallow and talipia.

Kits for Extraction and Purification of DNA
DNeasy@Tissue Kit (Qiagen, Hilden, Germany)
Equipment
PCR reactor: ABI PRISM 9700 Sequence Detector (Applied Biosystems, USA). Real-time PCR reactor: Light Cycler (Roche Applied Science, Mannheim, Germany).

Primers, Probe and Reaction Reagents

Chicken specific primer pairs and TaqMan probe for real-time PCR were designed according to the DNA sequence from DNA bank (see Table 1 below). For probes, 6-carboxyfluorescein was labeled in 5' ends and 6-carboxytetramethylrhodamine marker was labeled in 3' ends.

| Primer/Probe | Sequence 5'-3' | Specificity | Amplicon (bp) |
|---|---|---|---|
| Chicken | | | |
| CghF | TAACTTTTgTAAgCggACACTCAT | growth hormone/sense | |
| CghR | GCATTACCTgCgCTgTggC | growth hormone/antisense | 118 |
| CghP | FAM-CCTTCAggCTTgACAgTgACCTCCAg-TAMRA | growth hormone | |
| ChiF | GAgTggCCACATgTTATCTgC | 12S rRNA/sense | |
| ChiR | TAATCgTTgAggCTAAgATgg | 12S rRNA/antisense | 108 |

-continued

| Primer/Probe | Sequence 5'-3' | Specificity | Amplicon (bp) |
|---|---|---|---|
| ChiP | FAM-AgCCTAAgATCCACCTAAACCCAACCCA-TAMRA | | |

The kit used in the real PCR reaction is LightCycler-FastStart DNA Master Hybridization Probes (Roche Applied Science, Mannheim, Germany).

Conditions for PCR and Real-Time PCR Reactions

1. PCR Reaction Solution:

| | |
|---|---|
| 10x PCR Buffer Solution | 2.5 μL |
| Taq DNA polymerase (2 U/μL) | 1.0 μL |
| 2.5 mM dNTP | 4.0 μL |
| 10 μM primer F | 1.0 μL |
| 10 μM primer R | 1.0 μL |
| Template DNA Solution (100 ng) | 5.0 μL |
| Aseptic Pure Water | 10.5 μL |
| Total Volume | 25.0 μL |

2. PCR Setting Conditions:

| Step | Temperature | Time |
|---|---|---|
| 1. Initial Denaturation | 95° C. | 5 min |
| 2. Denaturation | 95° C. | 30 sec |
| 3. Annealing | 60° C. | 30 sec |
| 4. Extension/Elongation | 72° C. | 30 sec |
| Step 2 to 4, repeat 40 cycles | | |
| 5. Final Elongation | 72° C. | 7 min |

3. Real-Time PCR Reaction Solution:

| | |
|---|---|
| 5 μM primer F | 5 μL |
| 5 μM primer R | 1.5 μL |
| 3.3 μM primer P | 1.5 μL |
| LightCycler-FastStart DNA Master Hybridization Probes | 2.0 μL |
| 25 mM MgCl$_2$ Solution | 2.4 μL |
| Template DNA Solution (100 ng) | 5.0 μL |
| Aseptic Pure Water | 6.1 μL |
| Total Volume | 20.0 μL |

4. Real-Time PCR Conditions:

| Step | Temperature | Time |
|---|---|---|
| 1. Initial Denaturation | 95° C. | 10 min |
| 2. Denaturation | 95° C. | 5 sec |
| 3. Annealing | 60° C. | 25 sec |
| 4. Extension/Elongation | 72° C. | 8 sec |
| Step 2 to 4, repeat 45 cycles | | |
| 5. Cooling | 35° C. | 45 sec |

5. Detection Results

Figure 1:
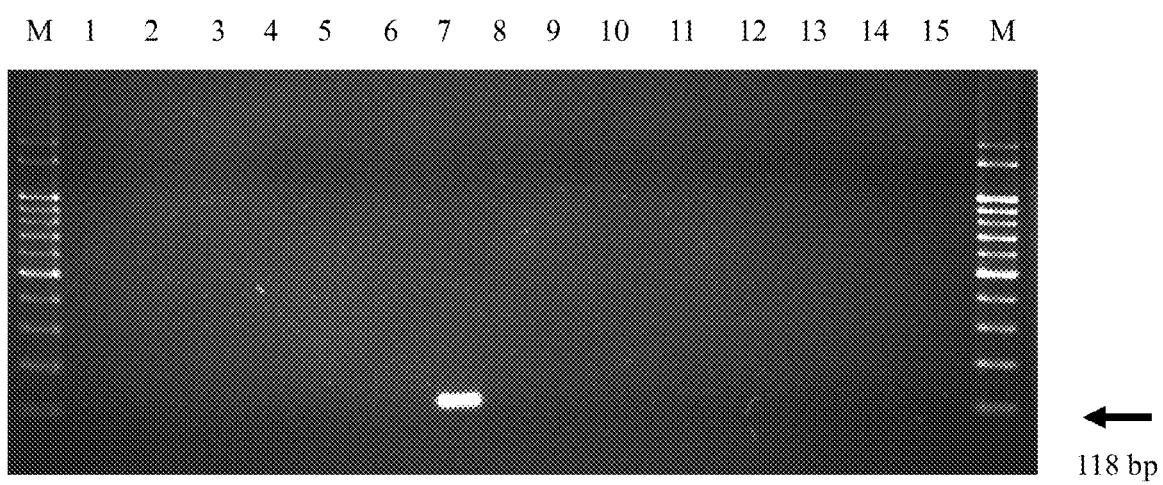
FIG. 1 shows the results of the specificity test of primer pair used to detect growth hormone gene in chicken. M: 100 bp marker; Lane 1: cattle; Lane 2: hog; Lane 3: kangaroo; Lane 4: goat; Lane 5: horse; Lane 6: deer; Lane 7: chicken; Lane 8: turkey; Lane 9: goose; Lane 10: ostrich; Lane 11: duck; Lane 12: rabbit; Lane 13: swallow; Lane 14: tilapia; Lane 15: NTC.
Figure 2:
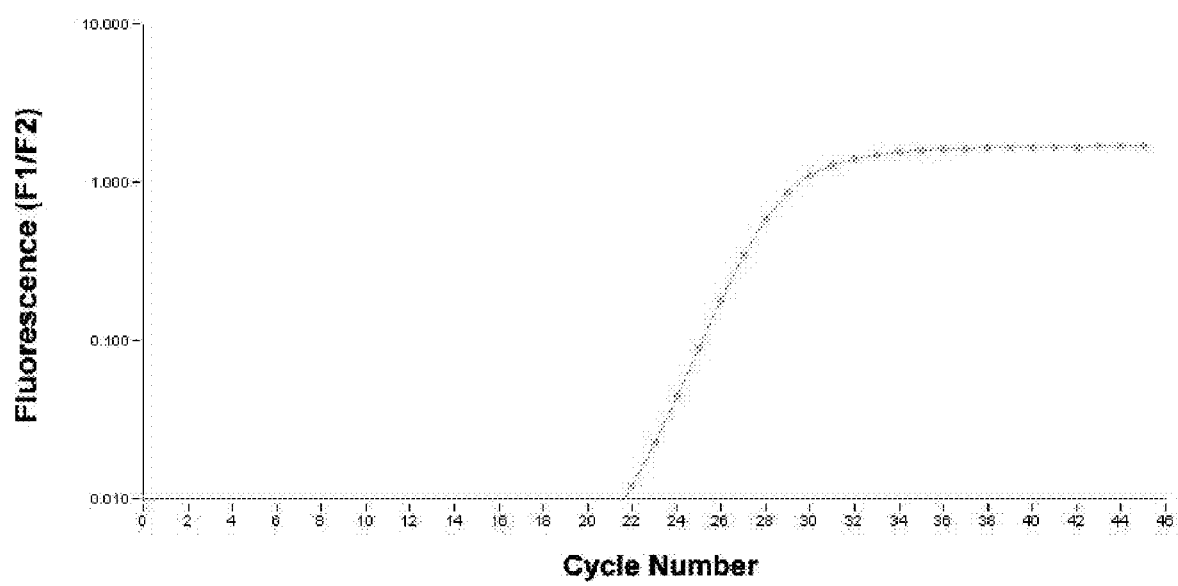
FIG. 2 shows the results of the specificity test of TaqMan probe used to detect growth hormone gene in chicken.
Figure 3:
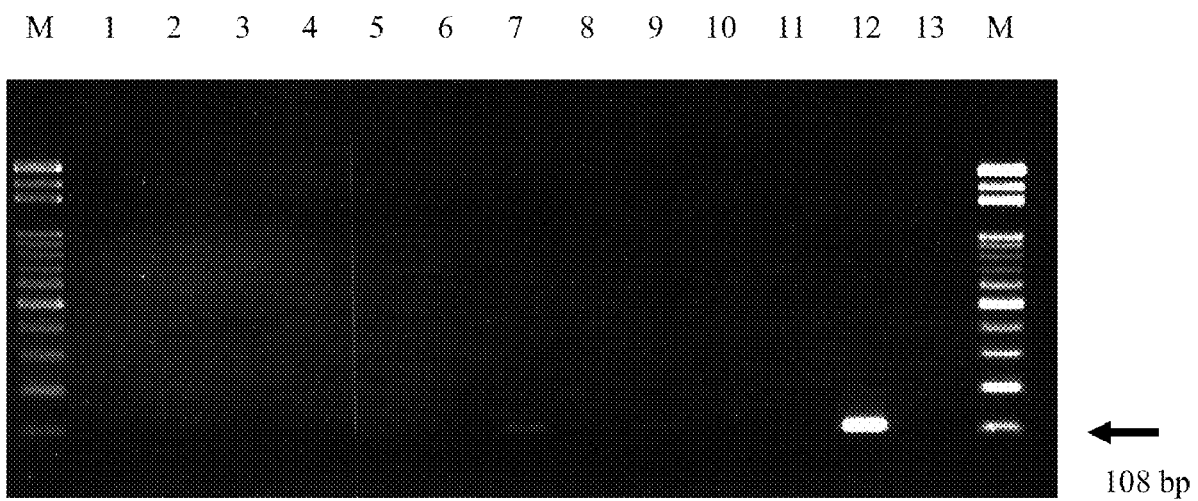
FIG. 3 shows the results of the specificity test of the primer pair used to detect 12S rRNA gene in chicken. M: 100 bp marker; Lane 1: cattle; Lane 2: hog; Lane 3: kangaroo; Lane 4: goat; Lane 5: horse; Lane 6: deer; Lane 7: duck; Lane 8: goose; Lane 9: ostrich; Lane 10: rabbit; Lane 11: turkey; Lane 12: chicken; Lane 13: NTC.
Figure 4:
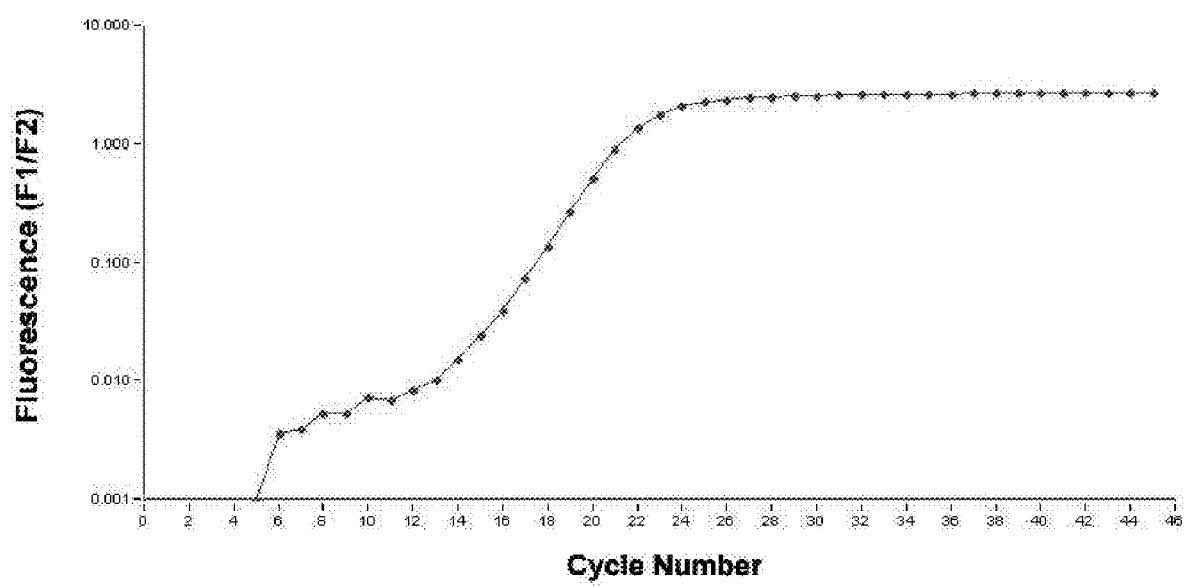
FIG. 4 shows the results of the specificity test of TaqMan probe used to detect 12S rRNA gene in chicken.

When primer pair specific to chicken growth hormone gene is used to perform PCR test, the result shows that only the chicken sample exhibits PCR amplification products among the 14 species tested (see FIG. 1). When primer pair and probe specific to chicken growth hormone gene are used to perform real time PCR test, the result shows that only chicken sample exhibits the PCR amplification curve on the plot of fluorescence signal versus cycle number among the 14 species tested (see FIG. 2). Also, when primer pair specific to chicken 12S rRNA gene is used to perform PCR test, the result show that only chicken sample exhibits PCR amplification products among 14 species tested (see FIG. 3). When primer pair and probe specific to chicken 12S rRNA gene are used to perform real time PCR test, only chicken sample exhibits the PCR amplification curve on the plot among the 14 species testd (see FIG. 4).

Example 2

Differentiation Between Chicken-Derived and Egg-Derived Ingredients

Samples

The samples tested in the example include chicken, egg yolk, egg white, 10 types of commercial meringue and commercial egg white powder.

Equipments

The DNA kits for extraction and purification are the same as those used in Example 1

Primers, Probe and Reaction Reagents

The primers, probes and reaction agents are the same as those used in Example 1.

Conditions for PCR and Real-Time PCR Reactions

The conditions for PCR and Real-Time PCR reactions are the same as those used in Example 1.

Detection Results

Figure 5:
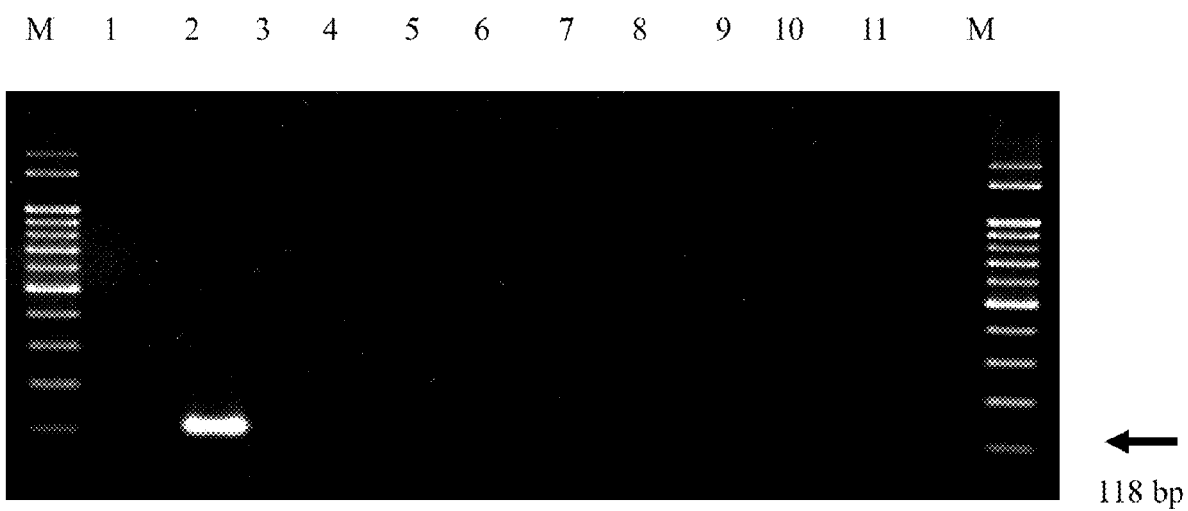
FIG. 5 shows the results of the detection of chicken, egg, commercial meringues and commercial egg white powder by specified growth hormone primer pair. M: 100 bp marker; Lane 1: NTC; Lane 2: chicken; Lane 3: egg; Lane 4: yolk; Lane 5: egg white; Lane 6: meringue 1; Lane 7: meringue 2.

When the primer pair specific to chicken growth hormone gene is used to perform PCR test, the result shows that among the 10 samples tested, only chicken exhibits amplification product (see FIG. 5). When the primer pair and probe specific to chicken growth hormone gene are used to perform real-Time PCR, the result shows that only the sample "chicken" exhibits strong PCR amplification curve. The Ct value of the curve is 22.47 cycle. The other 13 tested samples do not exhibit strong PCR amplification curves (see FIG. 6).

In the detection using designated primer pair and probe specific to chicken 12S rRNA, all samples tested exhibit PCR amplification products, but of different concentrations. (See FIG. 7, the concentration of PCR amplification products in lane 1 and 10 are too low to observed by the naked eye.) The real time PCR Ct values of the samples are as follow: chicken (13.72 cycle,) egg yolk (23.44 cycle,) egg (23.49 cycle,) commercial egg white powder (26.77 cycle,) egg white (29.70 cycle) and five types of commercial meringues (30.96-33.63 cycle) (see FIG. 8).

According to the test results described above, the Ct values of chicken are 22.47 cycle and 13.47 cycle when growth hormone gene specific and 12S rRNA gene specific primer pair and probe are respectively used to perform real time PCR. The difference in the Ct value is approximately 9 cycle, which means the copy number of the 12S rRNA gene is 500 times higher than the copy number of the growth hormone gene in chicken.

When 12S rRNA gene specific primer pair and probe are used to perform real time PCR, the Ct value of whole egg is 23.49. If the copy numbers of 12s rRNA gene and growth hormone gene are the same in chicken and egg, then the Ct value for growth hormone gene in chicken should be about 32.49. But the result of Real-Time PCR using primer pair and probe specific to growth hormone gene in egg did not show the amplification curve. Such result may have been caused by the very low copy number of growth hormone gene in egg. Therefore, it can be predicted that this is the reason why we were able to detect 12S rRNA gene but not growth hormone gene in this case.

The outcome of the above experiment matches with the expected/predicted results. Using the detection method of the invention to analyze the difference in copy numbers between the specific highly-conserved chicken chromosomal gene and mitochondrial gene in tested samples, one can successfully differentiate food products that only contain egg-derived ingredients from those contain other chicken-derived ingredients/parts/tissues.

What is claimed is:

1. A detection method to differentiate chicken-derived and egg-derived ingredients in food or products, said method comprising using primer pairs having the nucleotide sequences as shown in SEQ ID NO: 1 and SEQ ID NO: 2 specific for chicken growth hormone gene, and hybridized probe having the nucleotide sequence as shown in SEQ ID NO: 3 specific for chicken growth hormone gene, as well as primer pairs having the nucleotide sequences as shown in SEQ ID NO: 4 and SEQ ID NO: 5 specific for chicken 12S rRNA gene and hybridized probe having the nucleotide sequence as shown in SEQ ID No: 6 specific for chicken 12S rRNA gene, performing PCR and real time PCR to analyze the difference in DNA amount between the growth hormone gene and the 12S rRNA gene in samples;

determining that if the result shows that only the 12S rRNA but not the growth hormone gene is detected it means that the food or other product contains egg-derived ingredients but not chicken-derived ingredients, and if the 12S rRNA gene and the growth hormone gene are both detected, it means that the food or product contains chicken-derived ingredients.

2. The method according to claim 1, wherein the primer pairs specific for chicken growth hormone gene have nucleotide sequences consisting of SEQ ID NO: 1 and SEQ ID NO: 2.

3. The method according to claim 1, wherein the hybridized probe specific for chicken growth hormone has nucleotide sequence consisting of SEQ ID NO: 3.

4. The method according to claim 1, wherein the primer pairs specific for chicken 12S rRNA have nucleotide sequences consisting of SEQ ID NO: 4 and SEQ ID NO: 5.

5. The method according to claim 1, wherein the hybridized probe specific for chicken 12S rRNA gene has nucleotide sequences consisting of SEQ ID NO: 6.

* * * * *

SEQUENCE LISTING

```
<160> NUMBER OF SEQ ID NOS: 6

<210> SEQ ID NO 1
<211> LENGTH: 24
<212> TYPE: DNA
<213> ORGANISM: Artificial
<220> FEATURE:
<223> OTHER INFORMATION: synthesized nucleotide

<400> SEQUENCE: 1
taacttttgt aagcggacac tcat                                          24

<210> SEQ ID NO 2
<211> LENGTH: 19
<212> TYPE: DNA
<213> ORGANISM: Artificial
<220> FEATURE:
<223> OTHER INFORMATION: synthesized nueleotide

<400> SEQUENCE: 2
gcattacctg cgctgtggc                                                19

<210> SEQ ID NO 3
<211> LENGTH: 26
<212> TYPE: DNA
<213> ORGANISM: Artificial
<220> FEATURE:
<223> OTHER INFORMATION: synthesized nucleotide

<400> SEQUENCE: 3
ccttcaggct tgacagtgac ctccag                                        26

<210> SEQ ID NO 4
<211> LENGTH: 21
<212> TYPE: DNA
<213> ORGANISM: Artificial
<220> FEATURE:
<223> OTHER INFORMATION: synthesized nucleotide

<400> SEQUENCE: 4
gagtggccac atgttatctg c                                             21

<210> SEQ ID NO 5
<211> LENGTH: 21
<212> TYPE: DNA
<213> ORGANISM: Artificial
<220> FEATURE:
<223> OTHER INFORMATION: synthesized nucleotide

<400> SEQUENCE: 5
taatcgttga ggctaagatg g                                             21

<210> SEQ ID NO 6
<211> LENGTH: 28
<212> TYPE: DNA
```

-continued

```
<213> ORGANISM: Artificial
<220> FEATURE:
<223> OTHER INFORMATION: synthesized nucleotide

<400> SEQUENCE: 6
agcctaagat ccacctaaac ccaaccca                                             28
```